United States Patent
Zhang et al.

(10) Patent No.: US 10,503,970 B1
(45) Date of Patent: Dec. 10, 2019

(54) METHOD AND SYSTEM FOR IDENTIFYING BIOMETRIC CHARACTERISTICS USING MACHINE LEARNING TECHNIQUES

(71) Applicant: STATE FARM MUTUAL AUTOMOBILE INSURANCE COMPANY, Bloomington, IL (US)

(72) Inventors: Dingchao Zhang, Normal, IL (US); Michael Bernico, Bloomington, IL (US); Peter Laube, Bloomington, IL (US); Utku Pamuksuz, Champaign, IL (US); Jeffrey S. Myers, Normal, IL (US); Marigona Bokshi-Drotar, McKinney, TX (US); Edward W. Breitweiser, Bloomington, IL (US)

(73) Assignee: STATE FARM MUTUAL AUTOMOBILE INSURANCE COMPANY, Bloomington, IL (US)

( * ) Notice: Subject to any disclaimer, the term of this patent is extended or adjusted under 35 U.S.C. 154(b) by 63 days.

(21) Appl. No.: 15/837,522

(22) Filed: Dec. 11, 2017

(51) Int. Cl.
G06K 9/00 (2006.01)
G06K 9/62 (2006.01)
A61B 5/00 (2006.01)

(52) U.S. Cl.
CPC ........ *G06K 9/00362* (2013.01); *A61B 5/6891* (2013.01); *G06K 9/00711* (2013.01); *G06K 9/6256* (2013.01); *G06K 2009/00939* (2013.01)

(58) Field of Classification Search
CPC .......... G06K 9/00362; G06K 9/00711; G06K 9/6256; G06K 2009/00939; A61B 5/6891
See application file for complete search history.

(56) References Cited

U.S. PATENT DOCUMENTS

| | | |
|---|---|---|
| 9,769,420 B1 | 9/2017 | Moses |
| 2007/0073799 A1 | 3/2007 | Adjali et al. |
| 2008/0004904 A1 | 1/2008 | Tran |
| 2009/0024050 A1 | 1/2009 | Jung |
| 2014/0018097 A1 | 1/2014 | Goldstein |
| 2014/0121540 A1 | 5/2014 | Raskin |
| 2014/0297217 A1 | 10/2014 | Yuen |
| 2014/0333414 A1 | 11/2014 | Kursun |
| 2015/0054639 A1 | 2/2015 | Rosen |
| 2016/0022193 A1 | 1/2016 | Rau et al. |

(Continued)

OTHER PUBLICATIONS

U.S. Appl. No. 15/837,540, filed Dec. 11, 2017.

(Continued)

*Primary Examiner* — Leon Flores
(74) *Attorney, Agent, or Firm* — Marshall, Gerstein & Borun LLP; Randall G. Rueth

(57) ABSTRACT

A method and system may use computer vision techniques and machine learning analysis to automatically identify a user's biometric characteristics. A user's client computing device may capture a video of the user. Feature data and movement data may be extracted from the video and applied to statistical models for determining several biometric characteristics. The determined biometric characteristic values may be used to identify individual health scores and the individual health scores may be combined to generate an overall health score and longevity metric. An indication of the user's biometric characteristics which may include the overall health score and longevity metric may be displayed on the user's client computing device.

17 Claims, 8 Drawing Sheets

(56) References Cited

U.S. PATENT DOCUMENTS

| | | |
|---|---|---|
| 2016/0135706 A1 | 5/2016 | Sullivan et al. |
| 2017/0018008 A1 | 1/2017 | Hajiyev et al. |
| 2018/0106897 A1 | 4/2018 | Shouldice et al. |
| 2018/0289334 A1* | 10/2018 | De Brouwer ........ A61B 5/4872 |

OTHER PUBLICATIONS

Lapetus Solutions, Inc., Introducing Chronos (Jul. 2017).
Kocabey et al., Face-to-BMI: Using Computer Vision to Infer Body Mass Index on Social Media (Mar. 2017).
Ozbulak et al., How Transferable are CNN-based Features for Age and Gender Classification (2016).
Weber et al., Crowdsourcing Health Labels: Inferring Body Weight from Profile Pictures (Apr. 2016).
Office Action issued in U.S. Appl. No. 15/837,540 dated Aug. 12, 2019.

* cited by examiner

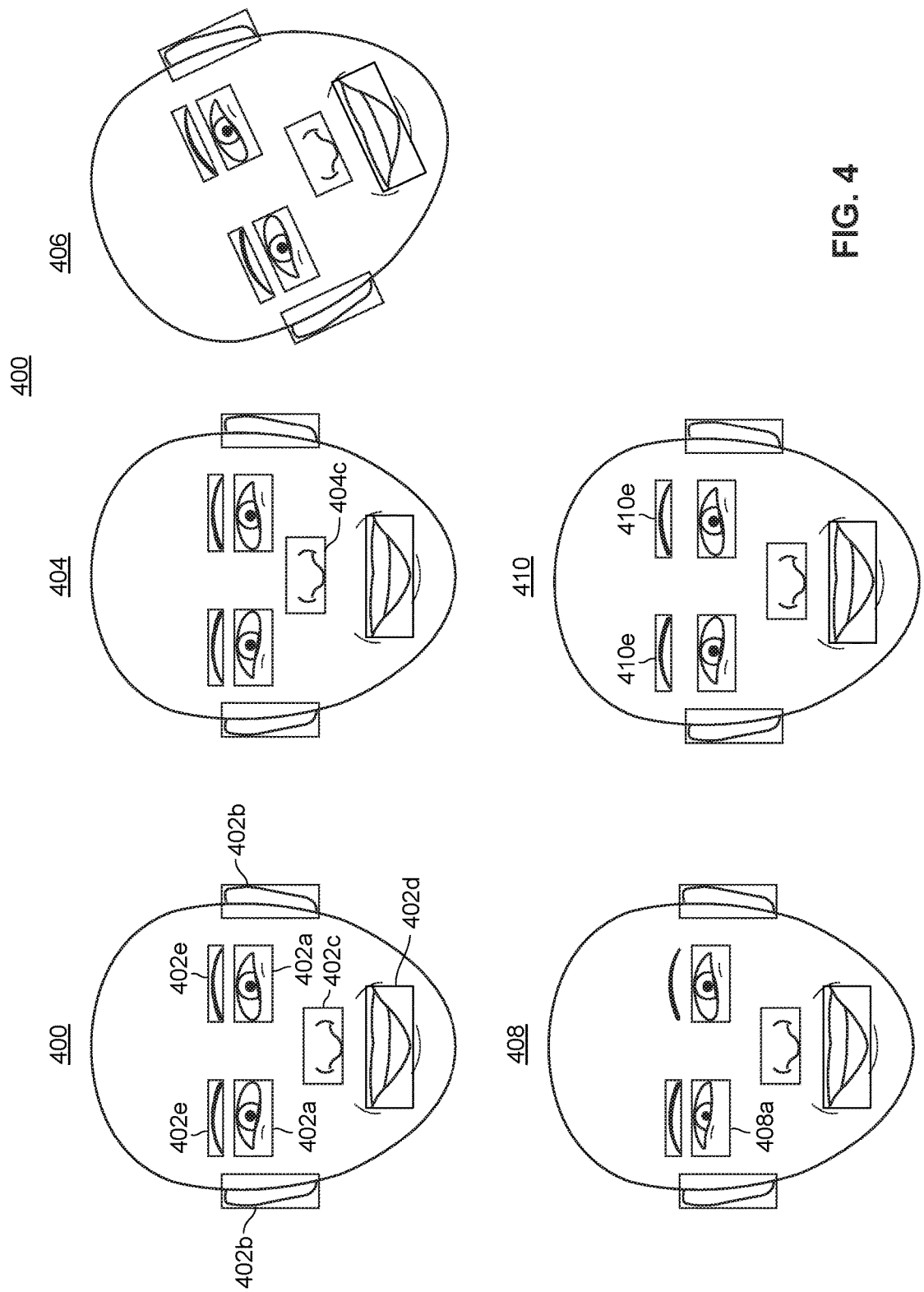

METHOD AND SYSTEM FOR IDENTIFYING BIOMETRIC CHARACTERISTICS USING MACHINE LEARNING TECHNIQUES

TECHNICAL FIELD

The present disclosure generally relates to identifying biometric characteristics and, more particularly to utilizing computer vision techniques and machine learning techniques to predict a user's biometric characteristics based on a video of the user.

BACKGROUND

Today, a user's health status may be determined based on several biometric characteristics, such as the user's age, gender, blood pressure, heart rate, body mass index (BMI), body temperature, stress levels, smoking status, etc. These biometric characteristics are typically obtained through self-reporting from the user (e.g., by filling out a form indicating the user's gender, birth date, etc.) and/or medical examinations that include taking measurements conducted by various instruments, such as a thermometer, scale, heart rate monitor, blood pressure cuff, etc.

This process of filling out forms and taking measurements with several different instruments may be difficult and time consuming for the user. Users may also withhold information or report incorrect information which may lead to inaccuracies in the health status assessment (e.g., from errors in self-reporting or uncalibrated instruments).

SUMMARY

To efficiently and accurately predict a user's health status and corresponding longevity metric, a biometric characteristic system may be trained using various machine learning techniques to create predictive models for determining biometric characteristics of the user based on video of the user. The determined or predicted biometric characteristics may be combined to generate an overall indication of the user's health which may be used to generate a longevity metric for the user. The biometric characteristic system may be trained by obtaining audiovisual data (e.g., videos or images) of several people having known biometric characteristics at the time the audiovisual data is captured (e.g., age, gender, BMI, etc.). The people may be referred to herein as "training subjects." For example, the training data may include public audiovisual data such as movies, television, music videos, etc., featuring famous actors or actresses having biometric characteristics which are known or which are easily obtainable through public content (e.g., via Internet Movie Database (IMDb®), Wikipedia™, etc.).

In some embodiments, the training data may include feature data extracted from the audiovisual data using computer vision techniques and the training data may include the known biometric characteristics that correspond to each set of feature data. In any event, the training data may be analyzed using various machine learning techniques to generate predictive models which may be used to determine biometric characteristics of a user, where the user's biometric characteristics are unknown to the system.

After the training period, a user may capture audiovisual data such as a video of herself via a client computing device and provide the video to the biometric characteristic system. The biometric characteristic system may analyze the video using computer vision techniques to identify a portion of each frame that corresponds to the user's face and to extract feature data from the identified portions. The extracted feature data for the user may be compared to the predictive models to determine the user's biometric characteristics. Additionally, the biometric characteristics may be used to determine an overall health indicator for the user and/or a longevity metric. Then the biometric characteristics, the overall health indicator, and/or the longevity metric may be provided for display on the user's client computing device.

In this manner, a user's health status may be predicted efficiently (e.g., in real-time or at least near-real time from when the video is provided to the biometric characteristic system) and accurately without relying on self-reporting, medical examinations, or readings from various instruments. The present embodiments advantageously streamline the health status assessment process and increase ease of use for users who may simply submit a short video clip of themselves instead of engaging in a lengthy process of filling out forms and providing medical records. Moreover, by capturing video rather than still images, the present embodiments advantageously extract movement data which may be used to predict additional biometric characteristics such as heart rate, blood pressure, galvanic skin response (GSR), etc. Furthermore, video may be more difficult for users to modify in attempts to alter their physical appearances, and therefore using video may prevent fraud.

In an embodiment, a method for identifying biometric characteristics of a user based on audiovisual data is provided. The method includes obtaining a plurality of sets of audiovisual data corresponding to a plurality of people and one or more biometric characteristics for each of the plurality of people. For each of the one or more biometric characteristics, the method includes analyzing the plurality of sets of audiovisual data to identify a plurality of features and generate a model for determining an unknown biometric characteristic of a user based on the plurality of features and the obtained biometric characteristic for each of the plurality of people. The method also includes receiving a set of audiovisual data corresponding to a user, wherein the audiovisual data includes a plurality of frames captured over a threshold time period, applying features within the set of audiovisual data corresponding to the user to the one or more models to determine the one or more biometric characteristics of the user, and providing an indication of the determined one or more biometric characteristics of the user to a client computing device.

In another embodiment, a server computing device for identifying biometric characteristics of a user based on audiovisual data is provided. The server computing device includes one or more processors and a non-transitory computer-readable memory coupled to the one or more processors and storing instructions thereon. When executed by the one or more processors, the instructions cause the server computing device to obtain a plurality of sets of audiovisual data corresponding to a plurality of people and one or more biometric characteristics for each of the plurality of people. For each of the one or more biometric characteristics, the instructions cause the server computing device to analyze the plurality of sets of audiovisual data to identify a plurality of features and generate a model for determining an unknown biometric characteristic of a user based on the plurality of features and the obtained biometric characteristic for each of the plurality of people. The instructions further cause the server computing device to receive a set of audiovisual data corresponding to a user, wherein the audiovisual data includes a plurality of frames captured over a threshold time period, apply features within the set of audiovisual data corresponding to the user to the one or more models to determine the one or more biometric characteristics of the user, and provide an indication of the determined one or more biometric characteristics of the user to a client computing device.

In yet another embodiment, a non-transitory computer-readable memory is provided. The computer-readable memory stores instructions thereon. When executed by one or more processors, the instructions cause the one or more processors to obtain a plurality of sets of audiovisual data corresponding to a plurality of people and one or more biometric characteristics for each of the plurality of people. For each of the one or more biometric characteristics, the instructions cause the one or more processors to analyze the plurality of sets of audiovisual data to identify a plurality of features and generate a model for determining an unknown biometric characteristic of a user based on the plurality of features and the obtained biometric characteristic for each of the plurality of people. The instructions further cause the one or more processors to receive a set of audiovisual data corresponding to a user, wherein the audiovisual data includes a plurality of frames captured over a threshold time period, apply features within the set of audiovisual data corresponding to the user to the one or more models to determine the one or more biometric characteristics of the user, and provide an indication of the determined one or more biometric characteristics of the user to a client computing device.

BRIEF DESCRIPTION OF THE DRAWINGS

The figures described below depict various aspects of the system and methods disclosed therein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

FIG. 4 illustrates an exemplary image analysis of feature data over several video frames in accordance with the presently described embodiments;

DETAILED DESCRIPTION

Figure 1:
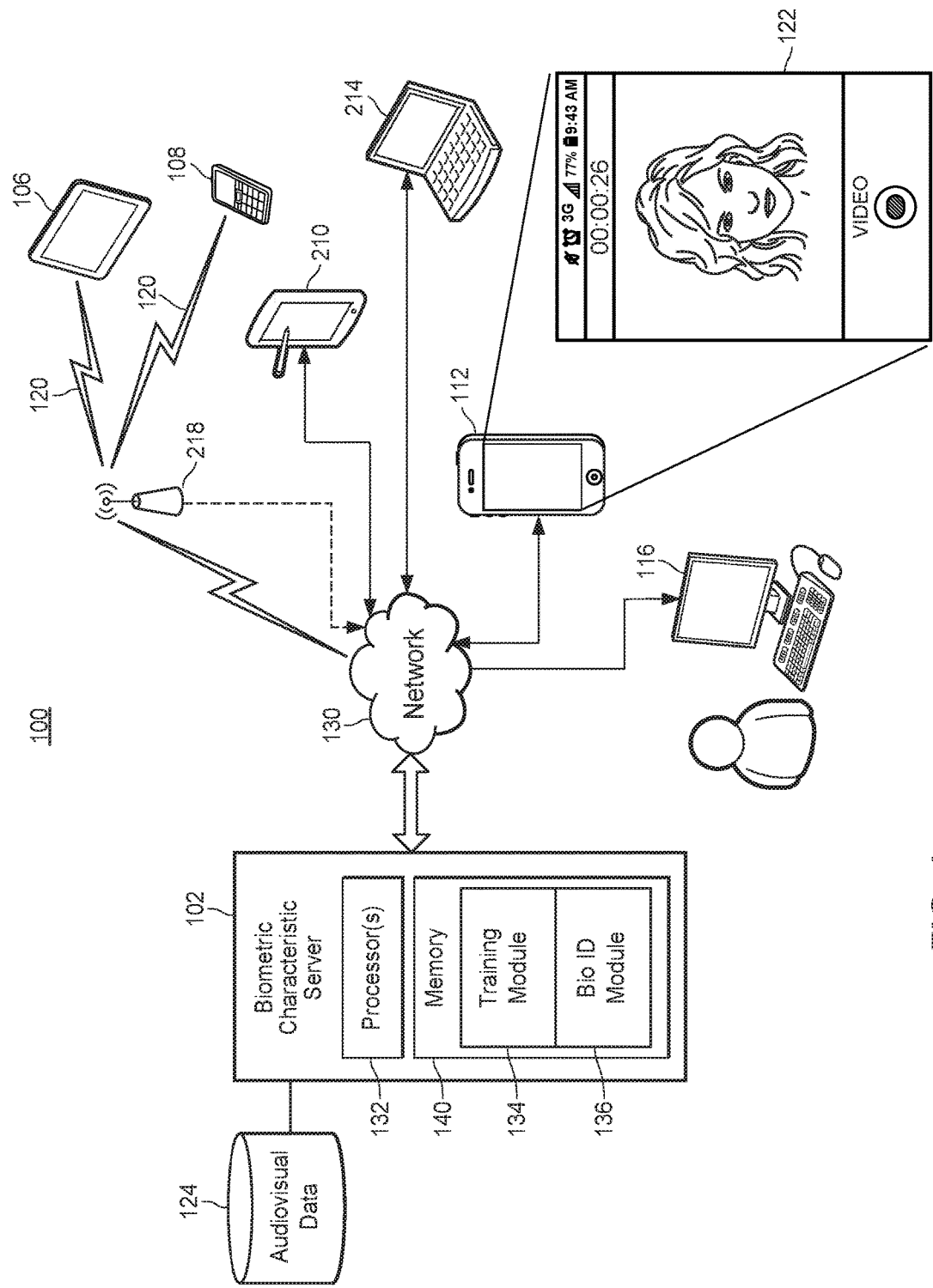
FIG. 1 illustrates a block diagram of a computer network and system on which an exemplary biometric characteristic system may operate in accordance with the presently described embodiments.

Although the following text sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments could be implemented, using either current technology or technology developed after the filing date of this patent, which would still fall within the scope of the claims.

It should also be understood that, unless a term is expressly defined in this patent using the sentence "As used herein, the term ' ' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, the patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

Accordingly, as used herein, the term "training subject" may refer to a person depicted in a video or other set of audiovisual data, where the person has biometric characteristics that are known to the system. For example, the training subject may be an actor or actress whose height, weight, age, gender, etc., may be retrieved from IMDb®, Wikipedia™, or any other suitable source of public content. Portions of each video frame depicting the training subject's face may be analyzed along with portions of other video frames depicting the faces of other training subjects to generate a statistical model for predicting a biometric characteristic based on the videos.

The term "feature" or "feature data" as used herein may be used to refer to an image feature extracted from a video frame or other image included in the audiovisual data. An image feature may include a line, edge, shape, object, etc. The feature may be described by a feature vector that includes attributes of the feature, such as RGB pixel values for the feature, the position of the feature within the face frame, the size of the feature relative to the face frame, the shape of the feature, the type of feature, pixel distances between the feature and other features, or any other suitable attributes.

The term "biometric characteristic" as used herein may refer to a biographical or physiological trait of a person, such as age, gender, BMI, blood pressure, heart rate, GSR, smoking status, body temperature, etc. Each biometric characteristic may correspond to a range of biometric characteristic values. For example, the biometric characteristic "age" may have biometric characteristic values from 1 to 120.

The term "longevity metric" as used herein may be used to refer to an estimate of the user's life expectancy or a remaining life expectancy for the user. The longevity metric may also be a monthly or yearly life insurance premium quote based on the remaining life expectancy for the user and/or other factors, such as the coverage amount, the policy type (e.g., term life insurance or whole life insurance), etc.

Generally speaking, techniques for determining biometric characteristics may be implemented in one or several client computing devices, one or several network servers or a system that includes a combination of these devices. However, for clarity, the examples below focus primarily on an embodiment in which a biometric characteristic server obtains a set of training data and uses the training data to generate statistical models for determining biometric characteristics of a user to generate a longevity metric for the user. The statistical models may be generated based on audiovisual data representing faces of training subjects having biometric characteristics known to the system and based on the known biometric characteristic values for each training subject. In some embodiments, the statistical models may be generated based on feature data included within the audiovisual data. Various machine learning techniques may be used to train the biometric characteristic server.

After the biometric characteristic server has been trained, a user may capture a video of herself taken over a threshold time period (e.g., five seconds, ten seconds, a minute, etc.) on the user's client computing device. The client computing device may transmit the video to the biometric characteristic server which may analyze the video frames to identify the user's face within each video frame. The biometric characteristic server may then identify feature data and may analyze the feature data using the machine learning techniques to determine biometric characteristics of the user. In some embodiments, the biometric characteristics server may use the biometric characteristics to determine a longevity metric for the user. An indication of the biometric characteristics and/or an indication of the longevity metric may be transmitted for display on the client computing device.

Referring to FIG. 1, an example biometric characteristic system 100 includes a biometric characteristic server 102 and a plurality of client computing devices 106-116 which may be communicatively connected through a network 130, as described below. According to embodiments, the biometric characteristic server 102 may be a combination of hardware and software components, also as described in more detail below. The biometric characteristic server 102 may have an associated database 124 for storing data related to the operation of the biometric characteristic system 100 (e.g., training data including audiovisual data such as video representing training subject's faces, feature data extracted from video frames, actual biometric characteristics for the training subjects, etc.). Moreover, the biometric server 102 may include one or more processor(s) 132 such as a microprocessor coupled to a memory 140.

The memory 140 may be tangible, non-transitory memory and may include any types of suitable memory modules, including random access memory (RAM), read-only memory (ROM), flash memory, other types of persistent memory, etc. The memory 140 may store, for example instructions executable on the processors 132 for a training module 134 and a biometric identification module 136. The biometric characteristic server 102 is described in more detail below with reference to FIG. 2A.

To generate statistical models for determining biometric characteristics, a training module 134 may obtain a set of training data by receiving videos or other audiovisual data of several training subjects where each video is captured over a threshold period of time. The video or other audiovisual data may be used to extract feature data from portions of the video frames that depict a training subject's face. The training module 134 may also obtain biometric characteristic values for the training subject. For example, the training subject may be a 35 year-old male having a BMI of 31 and blood pressure of 130/90. The training module 134 may then analyze the audiovisual data and known biometric characteristic values to generate a statistical model for a particular biometric characteristic (e.g., age). In some embodiments, the training module 134 may generate a statistical model for each of several biometric characteristics (e.g., age, gender, BMI, blood pressure, heart rate, GSR, smoking status, body temperature, etc.).

In any event, the set of training data may be analyzed using various machine learning techniques, such as neural networks, deep learning, naive Bayes, support vector machines, linear regression, polynomial regression, logistic regression, random forests, boosting, nearest neighbors, etc. In some embodiments, the statistical models may be generated using different machine learning techniques. For example, the statistical model for predicting age may be generated using deep learning and the statistical model for predicting gender may be generated using naive Bayes. In other embodiments, each statistical model may be generated using the same machine learning technique (e.g., deep learning). In a testing phase, the training module 134 may compare test audiovisual data for a test user to the statistical models to determine biometric characteristics of the test user.

If the training module 134 makes the correct determination more frequently than a predetermined threshold amount, the statistical model may be provided to a biometric identification module 136. On the other hand, if the training module 134 does not make the correct determination more frequently than the predetermined threshold amount, the training module 134 may continue to obtain training data for further training.

The biometric identification module 136 may obtain the statistical models for each biometric characteristic as well as audiovisual data for a user captured over a threshold period of time, such as a five-second video of the user. For example, the biometric identification module 136 may receive the audiovisual data from one of the client computing devices 106-116. The audiovisual data for the user may be compared to the statistical models to determine biometric characteristic values for the user. In some embodiments, the biometric identification module 136 may determine a likelihood that a biometric characteristic of the user is a particular value. For example, the biometric identification module 136 may determine there is a 70 percent chance the user is male and a 20 percent chance the user is female.

The biometric identification module 136 may then utilize the determined biometric characteristic values for the user or the likelihoods of biometric characteristic values to determine an overall health indicator for the user and/or a longevity metric for the user. For example, each biometric characteristic value may be associated with an individual health score. The individual health scores may be combined and/or aggregated in any suitable manner to determine an overall health score as the overall health indicator. In some embodiments, an individual health score may be determined using a lookup table based on the biometric characteristic value. The rules for determining the overall health score from the individual health scores may also be included in the lookup table. In other embodiments, the overall health score may be determined using machine learning techniques by generating a statistical model for determining the overall health score based on individual biometric characteristics or health scores. This is described in more detail below.

In any event, the overall health indicator may correspond to a particular longevity metric, where higher overall health indicators correspond to higher amounts of longevity. In some embodiments, the longevity metric may be an estimate of the user's life expectancy or a remaining life expectancy for the user. In other embodiments, the longevity metric may be a monthly or yearly life insurance premium quote based on the estimated amount of longevity for the user, the coverage amount, the policy type (e.g., term life insurance or whole life insurance), etc.

The biometric identification module 136 may transmit an indication of the biometric characteristics to one of the client computing devices 106-116 for display on a user interface. The indication may include the biometric characteristic values, the individual health scores, the overall health score, the longevity metric including a monthly or yearly life insurance premium quote, or any other suitable indication of the biometric characteristics of the user.

The client computing devices 106-116 may include, by way of example, various types of "mobile devices," such as a tablet computer 106, a cell phone 108, a personal digital assistant (PDA) 110, a smart phone 112, a laptop computer 114, a desktop computer 116, a portable media player (not shown), a home phone, a pager, a wearable computing device, smart glasses, smart watches or bracelets, phablets, other smart devices, devices configured for wired or wireless RF (Radio Frequency) communication, etc. Of course, any client computing device appropriately configured may interact with the biometric characteristic system 100. The client computing devices 106-116 need not necessarily communicate with the network 130 via a wired connection. In some instances, the client computing devices 106-116 may communicate with the network 130 via wireless signals 120 and, in some instances, may communicate with the network 130 via an intervening wireless or wired device 118, which may be a wireless router, a wireless repeater, a base transceiver station of a mobile telephony provider, etc.

Each of the client computing devices 106-116 may interact with the biometric characteristic server 102 to receive web pages and/or server data and may display the web pages and/or server data via a client application and/or an Internet browser (described below). For example, the smart phone 112 may display a video capturing screen 122, may capture video of a user, and may interact with the biometric characteristic server 102. For example, when a user captures video of herself, the video may be transmitted to the biometric characteristic server 102.

The biometric characteristic server 102 may communicate with the client computing devices 106-116 via the network 130. The digital network 130 may be a proprietary network, a secure public Internet, a local area network (LAN), a wide area network (WAN), a virtual private network (VPN) or some other type of network, such as dedicated access lines, plain ordinary telephone lines, satellite links, combinations of these, etc. Where the digital network 130 comprises the Internet, data communication may take place over the digital network 130 via an Internet communication protocol.

Figure 2A:
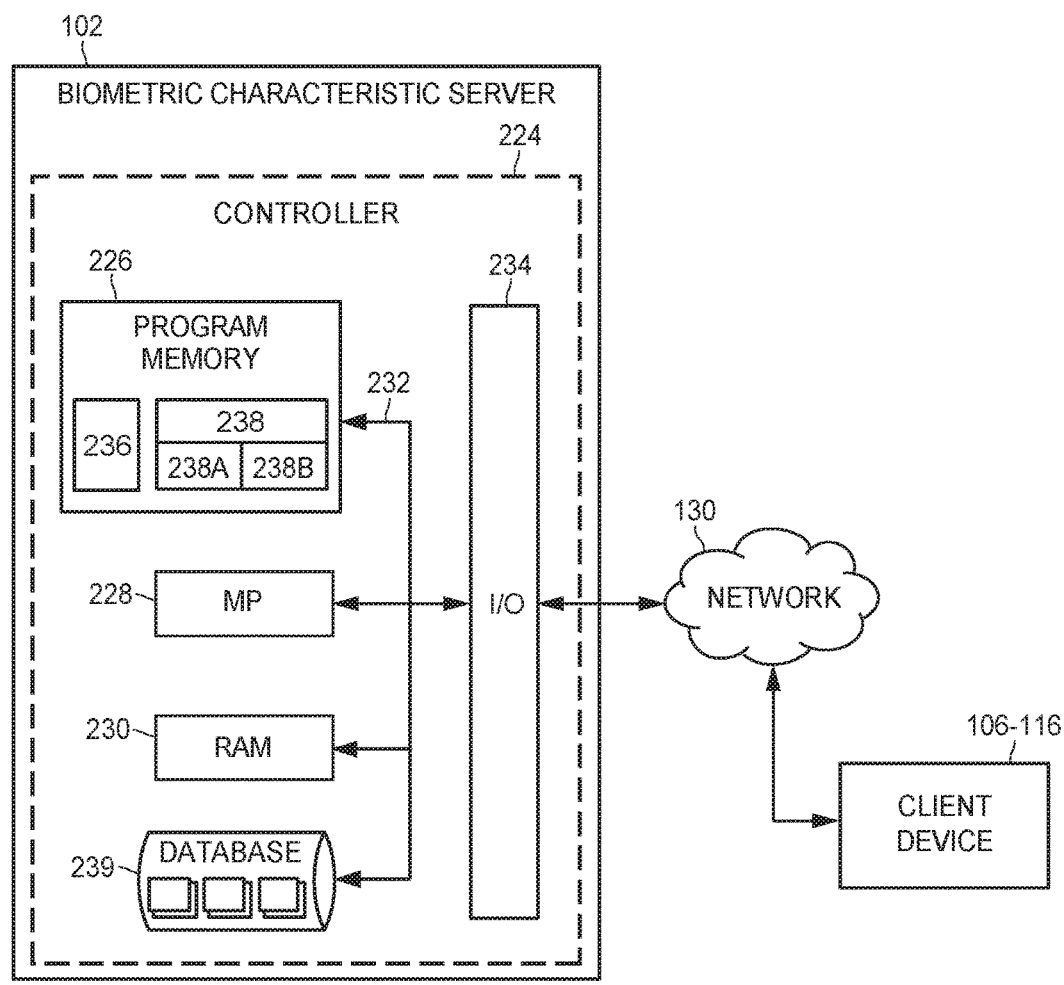
FIG. 2A illustrates a block diagram of an exemplary biometric characteristic server that can operate in the system of FIG. 1.

Turning now to FIG. 2A, the biometric characteristic server 102 may include a controller 224. The controller 224 may include a program memory 226, a microcontroller or a microprocessor (MP) 228, a random-access memory (RAM) 230, and/or an input/output (I/O) circuit 234, all of which may be interconnected via an address/data bus 232. In some embodiments, the controller 224 may also include, or otherwise be communicatively connected to, a database 239 or other data storage mechanism (e.g., one or more hard disk drives, optical storage drives, solid state storage devices, etc.). The database 239 may include data such as training data, web page templates and/or web pages, and other data necessary to interact with users through the network 130. It should be appreciated that although FIG. 2A depicts only one microprocessor 228, the controller 224 may include multiple microprocessors 228. Similarly, the memory of the controller 224 may include multiple RAMs 230 and/or multiple program memories 226. Although FIG. 2A depicts the I/O circuit 234 as a single block, the I/O circuit 234 may include a number of different types of I/O circuits. The controller 224 may implement the RAM(s) 230 and/or the program memories 226 as semiconductor memories, magnetically readable memories, and/or optically readable memories, for example.

As shown in FIG. 2A, the program memory 226 and/or the RAM 230 may store various applications for execution by the microprocessor 228. For example, a user-interface application 236 may provide a user interface to the biometric characteristic server 102, which user interface may, for example, allow a system administrator to configure, troubleshoot, or test various aspects of the server's operation. A server application 238 may operate to receive audiovisual data for a user, determine biometric characteristics of the user, and transmit an indication of the biometric characteristics to a user's client computing device 106-116. The server application 238 may be a single module 238 or a plurality of modules 238A, 238B such as the training module 134 and the biometric identification module 136.

While the server application 238 is depicted in FIG. 2A as including two modules, 238A and 238B, the server application 238 may include any number of modules accomplishing tasks related to implementation of the biometric characteristic server 102. Moreover, it will be appreciated that although only one biometric characteristic server 102 is depicted in FIG. 2A, multiple biometric characteristic servers 102 may be provided for the purpose of distributing server load, serving different web pages, etc. These multiple biometric characteristic servers 102 may include a web server, an entity-specific server (e.g. an Apple® server, etc.), a server that is disposed in a retail or proprietary network, etc.

Figure 2B:
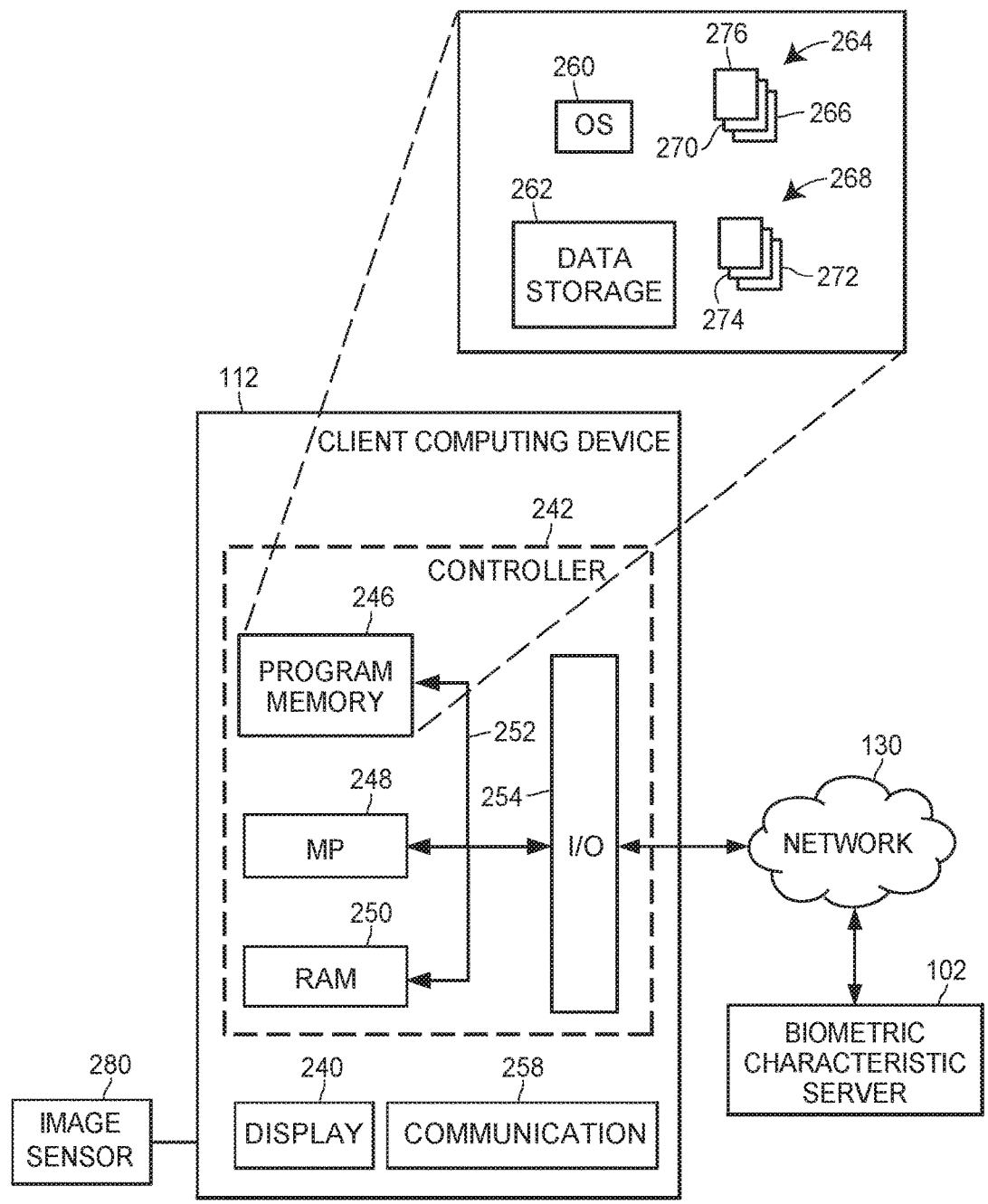
FIG. 2B illustrates a block diagram of an exemplary client computing device that can operate in the system of FIG. 1.

Referring now to FIG. 2B, the smart phone 112 (or any of the client computing devices 106-116) may include a display 240, a communication unit 258, accelerometers (not shown), a positioning sensor such as a Global Positioning System (GPS) (not shown), a user-input device (not shown), and, like the biometric characteristic server 102, a controller 242. The client computing device 112 may also include an image sensor 280 which may be a standard camera or a high resolution camera (e.g., having a resolution of greater than 30 Megapixels). In some embodiments, the image sensor 280 may be removably attached to the exterior of the client computing device 112. In other embodiments, the image sensor 280 may be contained within the client computing device 112. Also in some embodiments, the image sensor 280 may capture images and video and may be communicatively coupled to an audio sensor (not shown) such as a microphone and speakers for capturing audio input and providing audio output.

Similar to the controller 224, the controller 242 may include a program memory 246, a microcontroller or a microprocessor (MP) 248, a random-access memory (RAM) 250, and/or an input/output (I/O) circuit 254, all of which may be interconnected via an address/data bus 252. The program memory 246 may include an operating system 260, a data storage 262, a plurality of software applications 264, and/or a plurality of software routines 268. The operating system 260, for example, may include one of a plurality of mobile platforms such as the iOS®, Android™, Palm® webOS, Windows Mobile/Phone, BlackBerry® OS, or Symbian® OS mobile technology platforms, developed by Apple Inc., Google Inc., Palm Inc. (now Hewlett-Packard Company), Microsoft Corporation, Research in Motion (RIM), and Nokia, respectively.

The data storage 262 may include data such as user profiles, application data for the plurality of applications 264, routine data for the plurality of routines 268, and/or other data necessary to interact with the biometric characteristic server 102 through the digital network 130. In some embodiments, the controller 242 may also include, or otherwise be communicatively connected to, other data storage mechanisms (e.g., one or more hard disk drives, optical storage drives, solid state storage devices, etc.) that reside within the client computing device 112.

The communication unit 258 may communicate with the biometric characteristic server 102 via any suitable wireless communication protocol network, such as a wireless telephony network (e.g., GSM, CDMA, LTE, etc.), a Wi-Fi network (802.11 standards), a WiMAX network, a Bluetooth network, etc. The user-input device (not shown) may include a "soft" keyboard that is displayed on the display 240 of the client computing device 112, an external hardware keyboard communicating via a wired or a wireless connection (e.g., a Bluetooth keyboard), an external mouse, or any other suitable user-input device.

As discussed with reference to the controller 224, it should be appreciated that although FIG. 2B depicts only one microprocessor 248, the controller 242 may include multiple microprocessors 248. Similarly, the memory of the controller 242 may include multiple RAMs 250 and/or multiple program memories 246. Although the FIG. 2B depicts the I/O circuit 254 as a single block, the I/O circuit 254 may include a number of different types of I/O circuits. The controller 242 may implement the RAM(s) 250 and/or the program memories 246 as semiconductor memories, magnetically readable memories, and/or optically readable memories, for example.

The one or more processors 248 may be adapted and configured to execute any one or more of the plurality of software applications 264 and/or any one or more of the plurality of software routines 268 residing in the program memory 242, in addition to other software applications. One of the plurality of applications 264 may be a client application 266 that may be implemented as a series of machine-readable instructions for performing the various tasks associated with receiving information at, displaying information on, and/or transmitting information from the client computing device 112.

One of the plurality of applications 264 may be a native application and/or web browser 270, such as Apple's Safari®, Google Chrome™, Microsoft Internet Explorer®, and Mozilla Firefox® that may be implemented as a series of machine-readable instructions for receiving, interpreting, and/or displaying web page information from the server 102 while also receiving inputs from the user. Another application of the plurality of applications may include an embedded web browser 276 that may be implemented as a series of machine-readable instructions for receiving, interpreting, and/or displaying web page information from the biometric characteristic server 102. One of the plurality of routines may include a video capturing routine 272 which captures several video frames over a threshold time period (e.g., five seconds, ten seconds, a minute, etc.). Another routine in the plurality of routines may include a biometric characteristic display routine 274 which transmits the video to the biometric characteristic server 102 and presents an indication of the user's biometric characteristics based on the video of the user.

Preferably, a user may launch the client application 266 from the client computing device 112, to communicate with the biometric characteristic server 102 to implement the biometric characteristic system. Additionally, the user may also launch or instantiate any other suitable user interface application (e.g., the native application or web browser 270, or any other one of the plurality of software applications 264) to access the biometric characteristic server 102 to realize the biometric characteristic system.

Figure 3A:
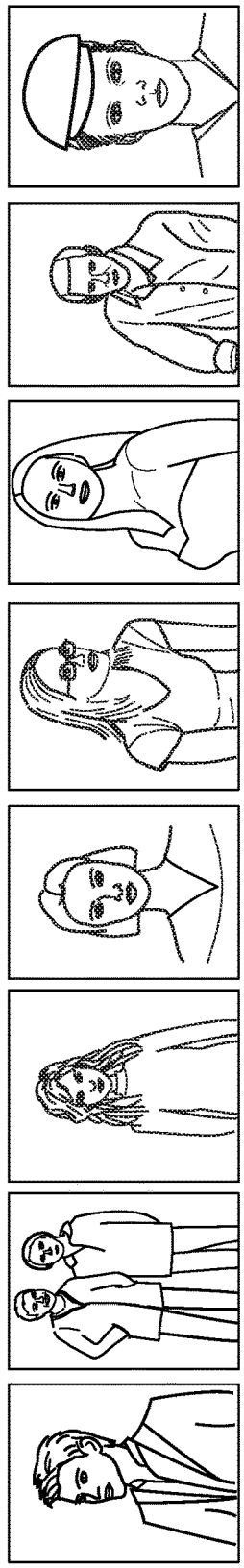
FIGS. 3A-B illustrate exemplary training data including video frames depicting faces which may be used for training a training module.

FIG. 3A depicts exemplary video frames 300 of training subjects having known biometric characteristics. Each of the video frames 300 may be from public audiovisual data such as movies, television, music videos, etc., featuring famous actors or actresses having biometric characteristics which are known or which are easily obtainable through public content (e.g., via IMDb®, Wikipedia™, etc.). For example, the first video frame 302 may depict John Doe who is a 40 year-old male and is 5'11" tall and weighs 170 pounds. Based on his height and weight John Doe's BMI is 23.7. The video frames 300 and known biometric characteristics may be stored in a database 124 and used as training data for the training module 134 as shown in FIG. 1 to generate statistical models for determining biometric characteristics. While the example video frames 300 include a single frame of each of several training subjects, the video frames 300 may include several frames of each training subject to detect movement data and/or identify additional features for each training subject. Several video frames of the same training subject may be stored in the database 124 in association with each other so that the biometric characteristic system 100 may analyze the several video frames together to identify movement, detect the boundaries of the training subject's face, or for any other suitable purpose.

Figure 3B:
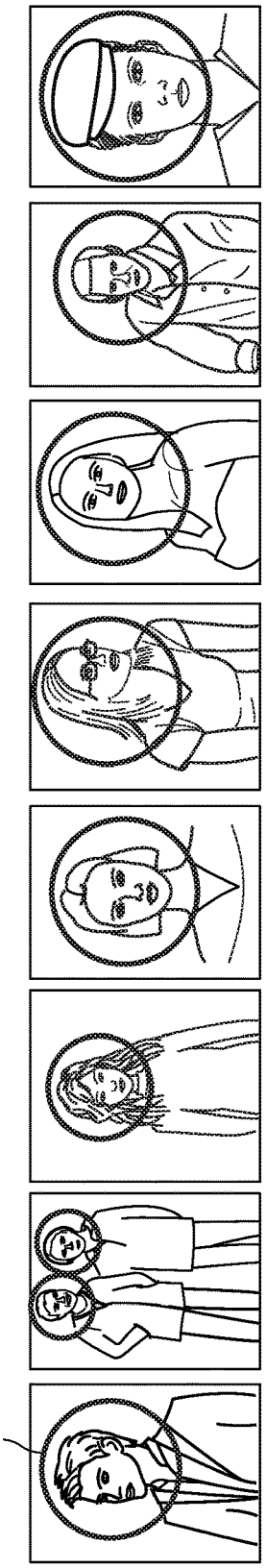

In some embodiments, each video frame 300 may be analyzed using face detection techniques to identify a portion of each video frame that depicts a training subject's face. Face detection techniques may include edge detection, pixel entropy, blink detection, motion detection, skin color detection, any combination of these, or any other computer vision techniques. FIG. 3B depicts example video frames 320 similar to the example video frames 300 annotated with outlines of the training subjects' faces. For example, the first video frame 302 depicting John Doe includes an elliptical annotation 322 around the boundaries of John's face. In some embodiments, the training module 134 may filter out the remaining portion of the video frame that does not include John Doe's face and may store the annotated portion of the video frame 322 in the database 124 for further analysis to generate the statistical models for determining biometric characteristics. The training module 134 may filter each of the video frames 320 and may store the annotated portions that depict the training subjects' faces.

Then each of the portions of the video frames depicting the training subjects' faces (referred to herein as "face frames") may be further analyzed to identify feature data within the face frames. Movement data may also be identified indicating a change in the positions of the feature data over multiple face frames for the same training subject. The feature data and the movement data for a training subject may then be stored in association with the biometric characteristics of the corresponding training subject. To generate a statistical model for a particular biometric characteristic (e.g., age), the training module 134 may obtain the feature data and movement data associated with different ages to identify particular sets of feature data and/or movement data that may be used to distinguish between ages (e.g., 45 or 55) or age ranges (e.g., 10-20 or 30-40). For example, while bones typically stop growing after puberty, cartilage such as ears and noses continue to grow throughout a person's life. Therefore, older people on average may have a larger ratio of the size of their ears and noses to the size of their heads than younger people. This ratio may be included in the feature data and used to distinguish between ages or age ranges. However, this is merely one example for ease of understanding. Additional or alternative feature data and movement data may be used to generate the statistical model for determining the age of a user based on audiovisual data.

Feature data may include edges such as the pixels in a face frame that depict the boundaries of a training subject's face or the boundaries of objects within the training subject's face, such as the boundaries of the training subject's eyes, nose, ears, mouth, cheeks, eyebrows, etc. Feature data may also include the portions of the face frame that depict different objects within the training subject's face, such as the training subject's eyes, nose, ears, mouth, cheeks, eyebrows, etc. Objects may be identified using edge detection or by identifying stable regions using a scale-invariant feature transform (SIFT), speeded up robust features (SURF), fast retina keypoint (FREAK), binary robust invariant scalable keypoints (BRISK), or any other suitable computer vision techniques. The feature data may include feature vectors that describe attributes of an object or edge, such as RGB pixel values for the object, the position of the object within the face frame, the size of the object relative to the face frame, the shape of the object, the type of object (e.g., nose, eyes, ears, mouth, etc.), or any other suitable attributes. Feature data may also include pixel distances between particular objects such as a mouth and nose.

Movement data may include the difference in the positions of features over multiple frames and/or the rate of change in the positions of the features. For example, video may be captured with a particular frame rate (e.g., 24 frames per second). If a particular features moves an average of 20 pixels over 48 frames the movement data may indicate that the features moved at a rate of 10 pixels per second.

FIG. 4 depicts an exemplary image analysis 400 of feature data over several video frames. In some embodiments, the image analysis 400 may be performed by the biometric characteristic server 102. For example, the video frames may be face frames 402-410 of training subject John Doe and the biometric characteristic server 102 may perform an image analysis of each face frame 402-410 to identify feature data and movement data over the set of face frames. In the first face frame 402, the biometric characteristic server 102 extracts several features including the training subject's eyes 402a, ears 402b, nose 402c, mouth 402d, and eyebrows 402e. The features may be stored as feature vectors that include attributes of each feature, such as RGB pixel values and corresponding positions of each pixel, the position of the feature within the face frame, the size of the feature relative to the face frame, the shape of the feature, the type of feature, etc. The feature data may also include distances between features, such as a distance between the training subject's eyes 402a or a distance between the training subject's eyes 402a and eyebrows 402e. Furthermore, the feature data may include other geometric properties such as ratios of sizes of features, lengths of features, widths of features, circumferences of features, diameters of features, or any other suitable properties.

In the image analysis 400, movement data may also be identified based on a change in position, orientation and/or size of one or several features over multiple face frames. For example, in the second face frame 404, a feature 404c may be identified having similar properties to the feature 402c in the first face frame 402, which may depict the training subject's nose. However, the feature 404c in the second face frame 404c may be higher than the feature 402c in the first face frame 402. Therefore, the movement data may indicate that the training subject's nose moved upward by a particular amount of pixels per frame or per second indicating that the training subject scrunched his nose. In some embodiments, movement data may be relative to changes in position, orientation and/or size of the other features. For example, in the third face frame 406, the training subject appears to tilt his head such that each of the features moves by the same or similar amount. From this frame, the movement data may indicate that the entire face moved, but the facial features did not move relative to each other.

The fourth and fifth face frames 408, 410 illustrate additional example movements which may be included in the movement data. More specifically, in the fourth frame 408 the training subject's right eye 408a is smaller than in the first frame 402 indicating the training subject may be squinting or winking. When both eyes decrease in size at the same time by a similar amount, the biometric characteristic server 102 may determine the training subject is blinking. In the fifth frame 410 the training subject's eyebrows 410e are higher than in the first frame 402 which may indicate that the training subject raised his eyebrows 410e.

For a particular biometric characteristic (e.g., gender), the training module 134 may classify the feature data and movement data into one of several subsets of training data, where each subset corresponds to a different biometric characteristic value (e.g., female) or range of biometric characteristic values (e.g., ages 20-29). Once each feature vector, movement vector, etc., is classified into one of the subsets, the training module 134 may analyze each of the subsets to generate a statistical model for determining the particular biometric characteristic. For example, when the machine learning technique is neural networks or deep learning, the training module 134 may generate a graph having input nodes, intermediate or "hidden" nodes, edges, and output nodes. The nodes may represent a test or function performed on feature data or movement data and the edges may represent connections between nodes. In some embodiments, the output nodes may include indications of biometric characteristic values for a particular biometric characteristic, such as a different age at each output node or likelihoods of biometric characteristic values, such as a likelihood of a particular age. In some embodiments, the edges may be weighted according to a strength of the test or function for the preceding node in determining the biometric characteristic.

For example, a neural network may include four input nodes representing different types of feature data and/or movement data, such as the shape of a feature, the size of the feature, an initial position of the feature within the face frame, and a change in position of the feature over a threshold number of frames. The input nodes may be connected to several hidden nodes that are connected to an output node indicating the user is 38 years old. The connections may have assigned weights and the hidden nodes may include tests or functions performed on the feature data and/or movement data. In some embodiments, the hidden nodes may be connected to several output nodes each indicating a different biometric characteristic value (e.g., a different age). However, this is merely one example of the inputs and resulting output of the statistical model for determining a biometric characteristic. In other examples, any number of input nodes may include several types of feature data and movement data. Additionally, any number of output nodes may provide different biometric characteristic values.

Moreover, while biometric characteristics such as age and gender may be predicted using feature data from a single face frame, more complex biometric characteristics such as BMI, GSR, blood pressure, body temperature, and heart rate may require movement data to generate accurate models. For example, heart rate may be determined based on subtle, periodic head motions due to the cyclical movement of blood from the heart to the head via the abdominal aorta and carotid arteries. Therefore, periodic frame-to-frame movements of a particular feature within the face frames, such as an object or edge that are within the frequency range of a typical heart rate (e.g., between 0.5 and 5 Hz) may be indicative of the user's heart rate. In this example, the periodic frame-to-frame movements of a particular feature may be included in input nodes of a neural network for determining heart rate and may be tested at intermediate or "hidden" nodes of the neural network. However, this is merely one example type of movement data that may be used to generate a statistical model for determining a particular biometric characteristic. Additional or alternative types of movement data may be used in combination with feature data from the training subjects to generate the statistical models for each biometric characteristic. In some embodiments, portions of face frames may be amplified or magnified to identify small frame-to-frame movements (e.g., a movement of a particular feature of one pixel or a half of a pixel).

As additional training data is collected, the weights, nodes, and/or connections may be adjusted. In this manner, the statistical models are constantly or periodically updated to reflect at least a near real-time representation of the feature data and/or movement data.

In addition to generating the statistical model based on feature data and movement data from face frames, the statistical model may also be generated based on biometric characteristics determined from other statistical models. For example, the statistical model for determining BMI may be based on feature data and movement data from face frames as well as age as determined by the statistical model for determining age. Moreover, the statistical model may be generated based on voice data from the training subjects. Some of the videos may include an audio component that includes a training subject's voice. Voice data may be indicative of certain biometric characteristics, such as smoking status. The voice data may include several voice components extracted from a training subject's speech such as frequency, pitch, intensity, tone, etc., which may be used as acoustic vectors in the statistical model. For example, a frequency analysis of the voice data may be performed (e.g., using a Fast Fourier Transformation (FFT) or other frequency transform) to identify the voice components. In this example, the statistical model for determining smoking status may be based on feature data and movement data from face frames as well as voice data including acoustic vectors. More specifically, the input nodes to the neural network for determining smoking status may include feature vectors for image features included in face frames, movement vectors indicative of the rate of change of the position or size of image features included in the face frames, and acoustic vectors indicative of the user's voice.

A statistical model may also be generated for determining emotional state. For example, the user's GSR may be indicative of stress levels of the user and thereby the user's emotional state. The user's GSR may also be combined with the user's heart rate and/or facial expressions identified in the feature and movement data of the face frames to identify the user's emotional state. In some embodiments, the statistical model for determining emotional state may be generated based on any suitable combination of GSR, heart rate, feature data, movement data, voice data, or any other biometric characteristic. As in the statistical models for determining biometric characteristics, the statistical model for determining emotional state may be trained using audiovisual data representing faces of training subjects having biometric characteristics known to the system and based on known emotional states of the training subjects. For example, the biometric characteristic server 102 may receive an indication that a first training subject suffers from clinical depression, a second training subject suffers from anxiety disorder, and a third training subject does not have any psychological disorders.

In any event, a statistical model may be generated for each biometric characteristic including age, gender, BMI, blood pressure, heart rate, GSR, smoking status, body temperature, etc. In addition to generating statistical models for determining biometric characteristics, the biometric characteristic server 102 may store lookup tables or a set of rules that correlate biometric characteristic values or a range of biometric characteristic values for a particular biometric characteristic with an individual health indicator or score. The user's emotional state may also be correlated with an individual health indicator or score. For example, people between the ages of 1-9 may be assigned an individual health score of 1; people between the ages of 10-19 may be assigned an individual health score of 2; people between the ages of 20-29 may be assigned an individual health score of 3, etc. The biometric characteristic server 102 may also store a lookup table or set of rules for combining individual heath indicators or scores to generate an overall health indicator or score indicative of the overall health of the user. For example, the individual health scores may be aggregated or averaged. In another example, the individual health scores may be weighted based on the corresponding biometric characteristic and then aggregated, multiplied, averaged, etc. More specifically, BMI may have less of an effect on overall health than blood pressure and thus, an individual health score assigned to blood pressure may be weighted higher than an individual health score assigned to BMI.

Furthermore, the biometric characteristic server 102 may store lookup tables or a set of rules that correlate overall health indicators or scores or ranges of overall health scores with a longevity metric, such as an estimate of the user's remaining life expectancy or longevity. For example, people with overall health scores above 90 may be expected to live 80 more years; people with overall heath scores between 80 and 89 may be expected to live 70 more years; people with overall health scores between 70 and 79 may be expected to live 60 more years, etc. The biometric characteristic server 102 may also store a set of rules for providing a monthly or yearly life insurance premium quote based on the user's remaining life expectancy, the coverage amount, and the policy type (e.g., term life insurance or whole life insurance).

In other embodiments, the individual health indicator or score, overall health indicator or score, and/or longevity metric may be determined using machine learning techniques based on the biometric characteristic values for training subjects and known health or longevity data for the training subjects.

In any event, the training module 134 may then test each statistical model generated using neural networks, deep learning, naive Bayes, support vector machines, linear regression, polynomial regression, logistic regression, random forests, boosting, nearest neighbors, or any other suitable machine learning technique. For example, the training module 134 may obtain test data including test video frames depicting a test subject and test biometric characteristics of the test subject. While the test biometric characteristics are known (e.g., the biometric characteristics of the test subject are provided to the biometric characteristic server 102 but the test video frames and test biometric characteristics are used for testing purposes), the training module 134 may determine a biometric characteristic value for each biometric characteristic for the test subject by extracting feature and movement data from the test video frames and comparing the feature and movement data to the respective statistical models.

For example, when a statistical model for determining BMI is a neural network, the training module 134 may traverse nodes of the neural network using the feature and movement data from the test video frames. After traversing each of the nodes which correspond to the test feature and movement data, the training module 134 may reach an output node which may indicate a BMI value, such as 21. The BMI value determined by the training module 134 may then be compared to the test BMI. In some embodiments, if the BMI value determined by the training module 134 is within a threshold amount of the test BMI (e.g., ±3), the determination may be deemed correct.

In any event, when the training module 134 is correct more than a predetermined threshold amount of time, the statistical model for the particular biometric characteristic may be provided to the biometric identification module 136. The statistical models for each biometric characteristic may be tested and presented to the biometric identification module 136. On the other hand, if the training module 134 does not correctly determine biometric characteristic values for a particular biometric characteristic more than the threshold amount, the training module 134 may continue obtaining sets of training data for training subjects to further train the statistical model corresponding to the particular biometric characteristic.

When each of the statistical models have been provided to the biometric identification module 136, the biometric identification module 136 may receive video or other audiovisual data from a user, where the user's biometric characteristics are unknown to the biometric characteristic server 102. Accordingly, the biometric identification module 136 may apply feature data and movement data from face frames included in the received video to each of the statistical models generated by the training module 134 to determine biometric characteristic values for the user and/or an emotional state of the user. The biometric characteristic values and/or emotional state may be used to determine individual health indicators or scores, which may in turn be used to determine an overall health indicator or score and a longevity metric. The longevity metric may include an estimate of the user's remaining life expectancy and/or a monthly or yearly life insurance premium quote based on the user's remaining life expectancy, a coverage amount, and a policy type (e.g., term life insurance or whole life insurance). The biometric identification module 136 may then provide an indication of the biometric characteristics to the user's client computing device 106-116 for display to the user. The indication may include the biometric characteristic values, the individual health scores, the overall health score, the longevity metric, or any suitable combination thereof. This is described in more detail below.

Figure 5:
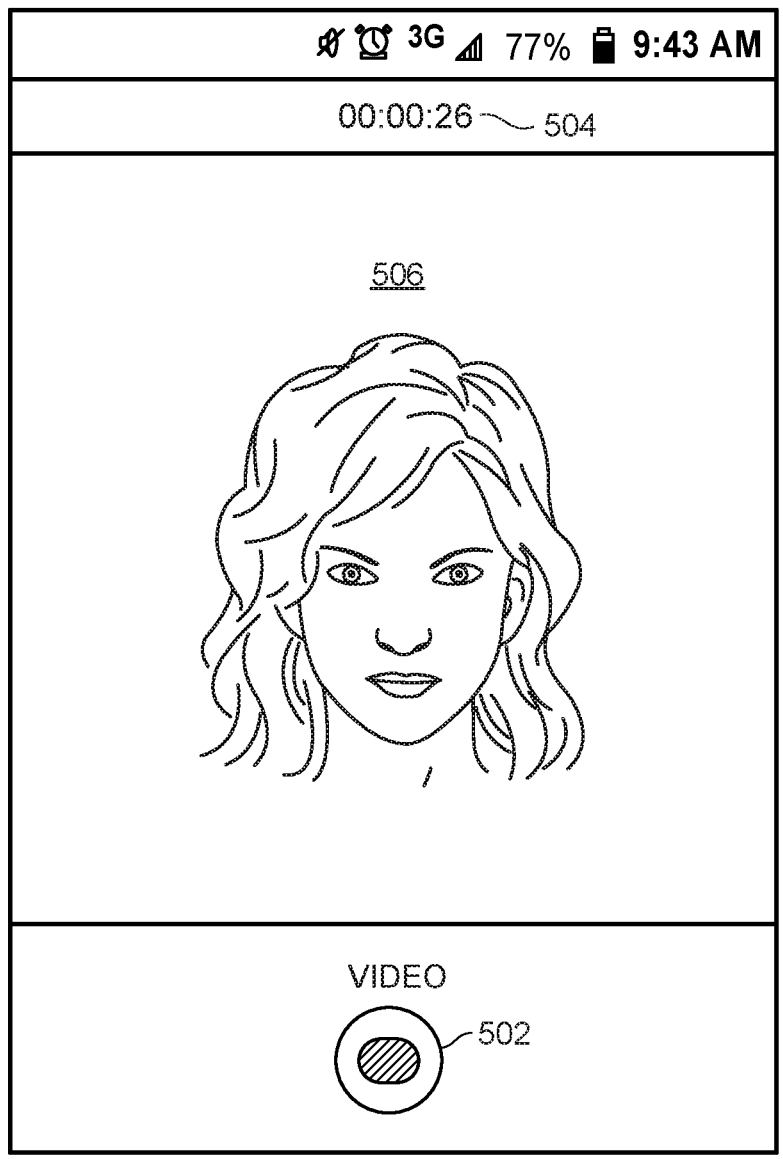
FIG. 5 illustrates an exemplary video capturing screen of a client application in accordance with the presently described embodiments.

FIG. 5 depicts an exemplary video capturing screen 500 which may be generated by the biometric characteristic server 102 and displayed by the client application 266 of the client computing device 112. In other embodiments, the exemplary screen may be generated and displayed by the client computing device 112. As will be appreciated by those of ordinary skill in the relevant art(s), the exemplary video capturing screen shown in FIG. 5 is for illustrative purposes, and the associated functionality may be implemented using any suitable format and/or design for facilitating corresponding described functionalities without departing from the spirit and scope of the present disclosure. In some embodiments, the biometric characteristic server 102 may transmit web pages.

The client application 266 may include a home screen (not shown) that prompts the user to capture video of herself to receive an indication of her biometric characteristics, health status, and/or longevity without filling out a form or providing textual information regarding her health. For example, the client application 266 may be associated with providing life insurance and the captured video may be provided instead of filling out a life insurance application. To receive a monthly or yearly life insurance premium quote, the user may simply capture a short video of herself (e.g., for five seconds, ten seconds, a minute, etc.) and provide the video to the biometric characteristic server 102 via a user control, such as a "Submit" button. The user may be requested to provide some information regarding the life insurance such as the policy type (e.g., term life insurance or whole life insurance) and the coverage amount (e.g., $500,000). The user may also be requested to speak during the video, so that the biometric characteristic server 102 may provide an audio analysis of the user's voice. In some embodiments, the user is prompted to state the policy type and coverage amount being requested during the video.

The home screen (not shown) may include user controls for capturing a new video or retrieving a video previously stored at the client computing device 112. The video capturing screen 500 may be presented in response to the user selecting the user control for capturing a new video. The video capturing screen 500 may include a record button 502 for starting and stopping the recording, a timer 504 indicating the length of time of the recording, and a camera view 506 presenting the video as it is being recorded. In some embodiments, the user may select the record button 502 once to start the recording and a second time to stop the recording. The client application 266 may provide instructions for the user to record for a particular amount of time (e.g., ten seconds), within a particular time range (e.g., between five and ten seconds), or for at least a threshold amount of time (e.g., five seconds). The user may stop the recording after a sufficient amount of time, as indicated by the timer 504. If the recording lasts for the particular amount of time, time range, or for at least the threshold amount of time, the client application 266 may present a user control (not shown) for providing the video to the biometric characteristic server 102, such as a "Submit" button. In some scenarios, the user may delete the recording and record a new video.

The biometric characteristic server 102 and more specifically, the biometric identification module 136 may receive the video and identify face frames within each video frame using face detection techniques as described above. Then the biometric identification module 136 may extract feature data and movement data from the face frames depicting the user and may apply the feature data and movement data to each of the statistical models for determining biometric characteristics and/or an emotional state of the user.

For example, when a statistical model for determining BMI is a neural network, the biometric identification module 136 may traverse nodes of the neural network using the feature and movement data from the face frames depicting the user. After traversing each of the nodes which correspond to the feature and movement data, the biometric identification module 136 may reach an output node which may indicate a BMI value, such as 32.

In some embodiments, the biometric identification module 136 may generate a user profile for the user and may store each of the determined biometric characteristics and/or emotional state for the user in the user profile. Also in some embodiments, the user may provide her name (e.g., in the video) and the name may also be stored in the user profile. In this manner, if the same user submits a subsequent video, the biometric characteristic server 102 may retrieve at least some of the user's biometric characteristics from her user profile. An image of the user such as a driver's license photograph may also be stored in the user profile and the image may be compared with the video frames to verify that the user is the person she claims to be. Additionally, the biometric characteristics stored in the user profile may be used as additional training data if it is determined that the biometric characteristics are accurate.

In any event, in response to providing the video to the biometric characteristic server 102 via the user control, the client application 266 may display a health status screen (not shown) which may include an indication of the biometric characteristics of the user as determined by the biometric characteristic server 102 via the statistical models. The indication of the biometric characteristics may include biometric characteristic values for the user. The indication of the biometric characteristics may also include an indication of the user's emotional state. For example, the health status screen may indicate the user is a 26 year-old female with a BMI of 19, a heart rate of 60 beats per minute, a blood pressure of 120/80, a body temperature of 98.2° F., etc. Furthermore, the indication of the biometric characteristics may include individual health scores for each of the biometric characteristics, an overall health score for the user, and a longevity metric such as the monthly or yearly life insurance premium quote for a particular policy type and coverage amount. The user may then purchase the life insurance via a user control such as an "Accept" button associated with the monthly or yearly life insurance premium quote.

In some embodiments, the user may review the biometric characteristic values and confirm that the biometric characteristic values are accurate via a user control or may edit the biometric characteristic values. For example, the health status screen may indicate the user is 31 years old. If she is in fact 29 years old, she may adjust her age via a text field or drop-down menu. Then the adjusted age may be provided to the biometric characteristic server 102 to recalculate her overall health score and longevity metric. If the biometric characteristic values are accurate then the overall health score and longevity metric may not need to be adjusted.

Additionally, when the user's overall health score is below a threshold amount or a particular biometric characteristic value is outside a threshold range, the client application 266 may display a warning or notification to the user and/or may advise the user to see a healthcare professional. In some embodiments, the user's emotional state may factor into the user's overall health indicator or longevity metric. For example, users who are depressed may have lower overall health scores. If the user is identified as depressed, suffering from another psychological disorder, or at risk for suicide according to the determined emotional state, the warning or notification may indicate to the user that she may be suffering from a psychological disorder and should seek help immediately. In some embodiments, upon receiving permission from the user, the biometric characteristic server 102 may send the warning or notification to emergency personnel or a healthcare professional identified by the user.

In other embodiments, the user does not provide the policy type and coverage amount and several life insurance premium quotes are provided for several different combinations of policy types and coverage amounts. For example, the client application 266 may display a table (not shown) where one column is for term life insurance, another column is for whole life insurance, each row is for a different coverage amount, and the entry corresponding to a particular row and column (e.g., whole life insurance for $100,000 of coverage) includes the monthly or yearly life insurance premium quote for the policy type and coverage amount.

In an exemplary scenario, Jane Smith would like to receive a life insurance premium quote for a whole life policy and a coverage amount of $1,000,000. Without providing any textual information regarding her health status or biographical information, Jane takes a ten second video of herself with her smart phone while explaining the type of life insurance policy she would like and the coverage amount in the video. The video is then provided to the biometric characteristic server and feature data and movement data extracted from face frames within the video are compared to statistical models for determining biometric characteristics using one or more of the machine learning techniques described above. The biometric characteristics are then applied to data from lookup tables or additional statistical models for determining a longevity metric for Jane Smith. Jane's smart phone may then receive and display a monthly or yearly life insurance premium quote for a whole life policy having a coverage amount of $1,000,000 based on her determined biometric characteristics. In this manner, Jane may receive a life insurance premium quote in real-time or at least near real-time upon providing the video and the biometric characteristic server may accurately determine her biometric characteristics, thereby reducing the risk of obtaining false information.

Additionally, if any of Jane's biometric characteristics are outside of a healthy range (e.g., a predetermined range of acceptable values) or more than a threshold variance from the healthy range, she may receive a notification indicating the biometric characteristic that is outside of the healthy range, the corresponding biometric characteristic value, and/or an indication of the healthy range. The notification may also advise her to see a healthcare professional. If Jane's emotional state indicates she is suffering from a psychological disorder, she may receive a notification indicating the psychological disorder and a recommendation to see a healthcare professional.

Figure 6:
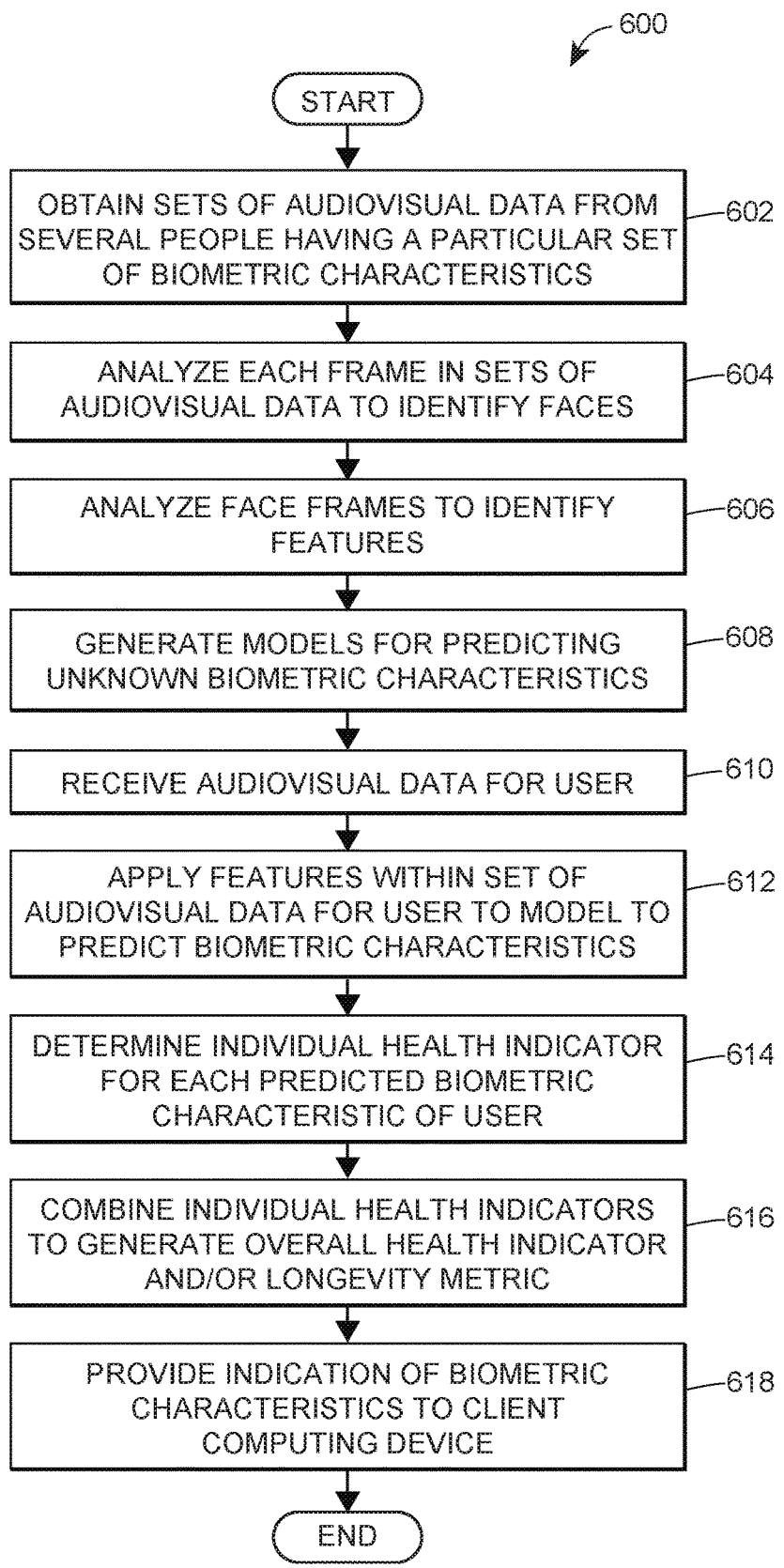
FIG. 6 illustrates a flow diagram representing an exemplary method for identifying biometric characteristics of a user based on audiovisual data in accordance with the presently described embodiments.

FIG. 6 depicts a flow diagram representing an exemplary method 600 for identifying biometric characteristics of a user based on audiovisual data. The method 600 may be executed on the biometric characteristic server 102. In some embodiments, the method 600 may be implemented in a set of instructions stored on a non-transitory computer-readable memory and executable on one or more processors of the biometric characteristic server 102. For example, the method 600 may be performed by the training module 134 and the biometric identification module 136 of FIG. 1.

At block 602, the biometric characteristic server 102 and more specifically, the training module 134 may obtain training data including sets of audiovisual data of training subjects having known biometric characteristics at the time the audiovisual data is captured (e.g., age, gender, BMI, etc.). The training data may include public audiovisual data such as movies, television, music videos, etc., featuring famous actors or actresses having biometric characteristics which are known or which are easily obtainable through public content (e.g., via IMDb®, Wikipedia™, etc.). In some embodiments, the emotional states of the training subjects may also be obtained.

A set of audiovisual data for a training subject may be a video of the training subject that includes several video frames. In some embodiments, each video frame may be analyzed using face detection techniques to identify a portion of each video frame that depicts a training subject's face (a face frame) (block 604). Face detection techniques may include edge detection, pixel entropy, blink detection, motion detection, skin color detection, any combination of these, or any other computer vision techniques. In some embodiments, the training module 134 may filter out the remaining portion of the video frame that does not include the training subject's face.

At block 606, each face frame may be further analyzed to identify feature data within the face frames. Movement data may also be identified indicating a change in the positions or sizes of features over multiple face frames for the same training subject. Feature data may include edges such as the pixels in a face frame that depict the boundaries of a training subject's face, the boundaries of objects, or the objects within the training subject's face. Objects may be identified using edge detection or by identifying stable regions using a scale-invariant feature transform (SIFT), speeded up robust features (SURF), fast retina keypoint (FREAK), binary robust invariant scalable keypoints (BRISK), or any other suitable computer vision techniques. The feature data may include feature vectors that describe attributes of an object or edge, such as RGB pixel values for the object, the position of the object within the face frame, the size of the object relative to the face frame, the shape of the object, the type of object (e.g., nose, eyes, ears, mouth, etc.), or any other suitable attributes. Feature data may also include pixel distances between particular objects such as a mouth and nose.

Movement data may include the difference in the positions of features over multiple frames and/or the rate of change in the positions of the features. For example, video may be captured with a particular frame rate (e.g., 24 frames per second). If a particular features moves an average of 20 pixels over 48 frames the movement data may indicate that the features moved at a rate of 10 pixels per second.

The feature data and the movement data for a training subject may then be stored in association with the biometric characteristics of the corresponding training subject. In some embodiments, voice data may also be included within the videos and the training module 134 may extract voice components from a training subject's speech such as frequency, pitch, intensity, tone, etc.

Then at block 608, a statistical model may be generated for determining each of the biometric characteristics (e.g., age, gender, BMI, blood pressure, heart rate, GSR, smoking status, body temperature, etc.) by analyzing the training data using various machine learning techniques, such as neural networks, deep learning, naive Bayes, support vector machines, linear regression, polynomial regression, logistic regression, random forests, boosting, nearest neighbors, etc. For a particular biometric characteristic (e.g., gender), the training module 134 may classify the feature data, movement data, audio data, or biometric characteristic value for another biometric characteristic (e.g., BMI) into one of several subsets of training data, where each subset corresponds to a different biometric characteristic value (e.g., female) or range of biometric characteristic values. Once each feature vector, movement vector, acoustic vector, etc., is classified into one of the subsets, the training module 134 may analyze each of the subsets to generate a statistical model for determining the particular biometric characteristic.

In addition to generating statistical models for determining each of the biometric characteristics using machine learning techniques, the training module 134 may generate a statistical model for determining emotional state using machine learning techniques. In some embodiments, the statistical model for determining emotional state may be generated based on any suitable combination of GSR, heart rate, feature data, movement data, voice data, or any other biometric characteristic.

The training module 134 may also obtain correlations between biometric characteristics and/or emotional state and individual health indicators or scores from lookup tables, a set of rules, or statistical models using machine learning techniques. Further, the training module 134 may obtain a set of rules for generating an overall health indicator or score and a longevity metric based on the individual health indicators or scores from a lookup table or statistical models using machine learning techniques.

At block 610, the biometric identification module 136 may receive a set of audiovisual data for the user, such as video of the user captured for a threshold time period, where the user's biometric characteristics are unknown to the biometric characteristic server 102. For example, the biometric identification module 136 may receive a video such as the video captured by the video capturing screen 500 as shown in FIG. 5.

The biometric identification module 136 may then identify face frames within each video frame using the face detection techniques described above and extract feature data and movement data from the face frames depicting the user. The biometric identification module 136 may also obtain voice data from the video. Then the biometric identification module 136 may apply the feature data, movement data, and voice data to one of the statistical models for determining a particular biometric characteristic (block 612). This may be repeated for each of the statistical models to determine each of the biometric characteristics and the emotional state of the user. In some embodiments, a determined biometric characteristic value for one biometric characteristic (e.g., age) may be applied to a statistical model for determining another biometric characteristic (e.g., BMI).

At block 614, the biometric identification module 136 may determine individual health indicators or scores from the determined biometric characteristics and/or emotional state using the correlations or statistical model obtained by the training module 134. The individual health indicators or scores may be combined or aggregated to generate an overall health indicator and/or longevity metric using the set of rules or statistical model obtained by the training module 134 (block 616).

Then the biometric identification module 136 may provide an indication of the biometric characteristics for display on the user's client computing device (block 618). The indication may include biometric characteristic values for the user. The indication of the biometric characteristics may also include an indication of the user's emotional state. Furthermore, the indication of the biometric characteristics may include individual health scores for each of the biometric characteristics, an overall health score for the user, and a longevity metric such as the monthly or yearly life insurance premium quote for a particular policy type and coverage amount. For example, the indication of the biometric characteristics may be presented on a health status screen of a client application 266 on the user's client computing device, as described above with reference to FIG. 5. In some embodiments, the biometric identification module 136 may also provide a warning or notification for display on the user's client computing device when the user's overall health score is below a threshold amount, a particular biometric characteristic value is outside a threshold range, or the user is identified as suffering from a psychological disorder.

Figure 7:
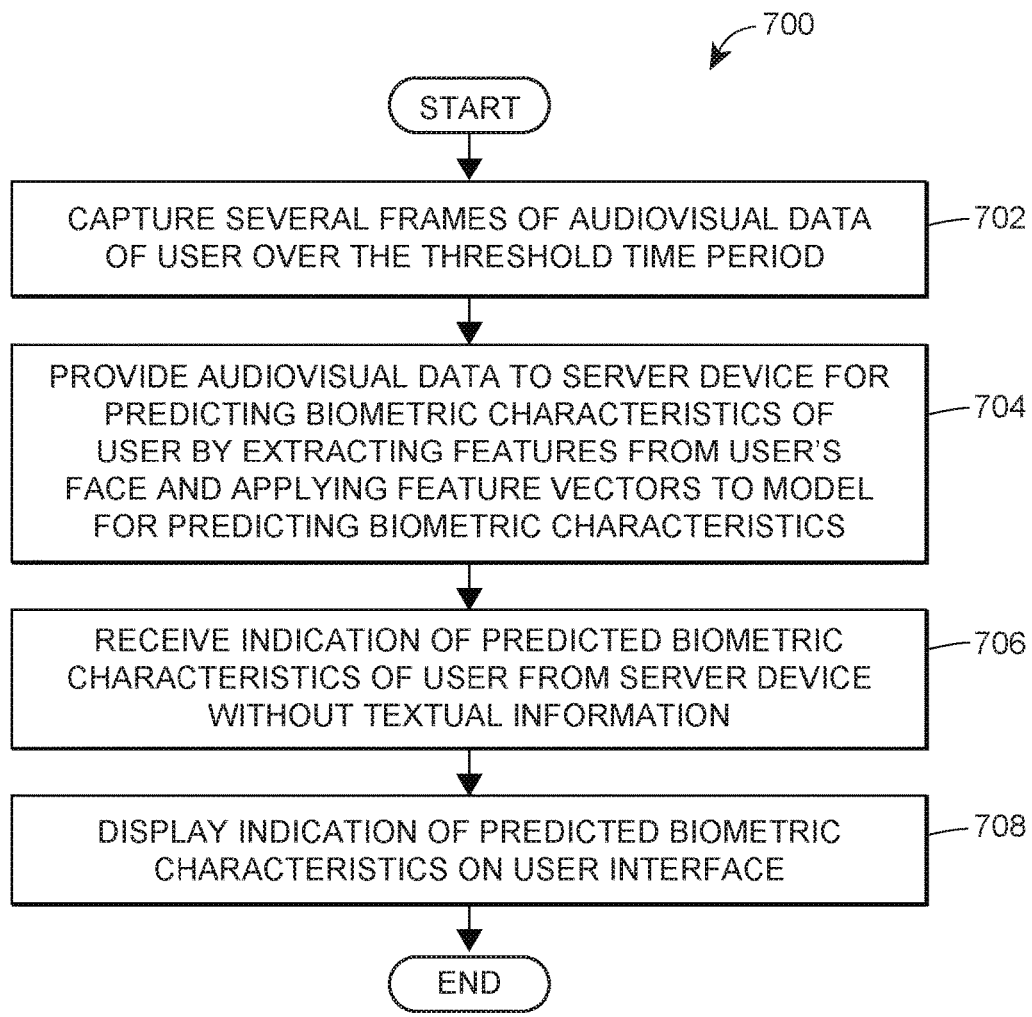
FIG. 7 illustrates a flow diagram representing an exemplary method for capturing audiovisual data representing a user and presenting indications of automatically determined biometric characteristics of the user in accordance with the presently described embodiments.

FIG. 7 depicts a flow diagram representing an exemplary method 700 for capturing audiovisual data representing a user and presenting indications of automatically determined biometric characteristics of the user. The method 700 may be executed on the client computing device 112. In some embodiments, the method 700 may be implemented in a set of instructions stored on a non-transitory computer-readable memory and executable on one or more processors of the client computing device 112. For example, the method 700 may be performed by the client application 266. In other embodiments, the method 700 may be performed by the biometric characteristic server 102 and/or a combination of the client computing device and the biometric characteristic server 102.

At block 702, the client computing device 112 and more specifically, the client application 266 may capture video of a user over a threshold time period. For example, the video may be captured via the video capturing screen 500 as shown in FIG. 5. In some embodiments, a home screen of the client application 266 may include user controls for capturing a new video or retrieving a video previously stored at the client computing device 112. The client application 266 may also provide instructions for the user to record for the threshold time period (e.g., five seconds) and/or may provide instructions for the user to speak and answer questions, such as the user's name, the policy type being requested, and the amount of coverage being requested. If the recording lasts for the threshold time period, the client application 266 may present a user control for providing the video to the biometric characteristic server 102, such as a "Submit" button.

At block 704, the video is transmitted to the biometric characteristic server 102, which may in turn analyze the video frames and voice data to extract feature data and movement data within face frames and voice components from the user's speech such as frequency, pitch, intensity, tone, etc. The biometric characteristic server 102 may then apply feature vectors, movement vectors, and acoustic vectors to statistical models for determining biometric characteristics and an emotional state of the user. The biometric characteristic server 102 may also determine individual health indicators or scores, an overall health indicator or score, and a longevity metric based on the determined biometric characteristics and emotional state of the user.

At block 706, the client computing device 112 receives an indication of the biometric characteristics of the user from the biometric characteristic server 102 without providing textual information to the biometric characteristic server 102. The indication may include biometric characteristic values for the user, an indication of the user's emotional state, individual health scores for each of the biometric characteristics, an overall health score for the user, and/or a longevity metric such as the monthly or yearly life insurance premium quote for a particular policy type and coverage amount.

Then the client computing device 112 presents the indication of the biometric characteristics on the user interface 240. For example, the client application 266 may include a health status screen which displays the indication of the user's biometric characteristics. For example, the health status screen may indicate the user is a 26 year-old female with a BMI of 19, a heart rate of 60 beats per minute, a blood pressure of 120/80, a body temperature of 98.2° F., etc. The health status screen may also indicate that for a whole life insurance policy and a coverage amount of $50,000, the yearly life insurance premium will be $700. The user may then purchase the life insurance via a user control on the health status screen such as an "Accept" button associated with the monthly or yearly life insurance premium quote.

In some embodiments, the user may review the biometric characteristic values and confirm that the biometric characteristic values are accurate via a user control or may edit the biometric characteristic values. For example, the health status screen may indicate the user is 31 years old. If she is in fact 29 years old, she may adjust her age via a text field or drop-down menu. Then the adjusted age may be provided to the biometric characteristic server 102 to recalculate her overall health score and longevity metric. If the biometric characteristic values are accurate then the overall health score and longevity metric may not need to be adjusted.

Additionally, when the user's overall health score is below a threshold amount, a particular biometric characteristic value is outside a threshold range, or the user's emotional state indicates the user is suffering from a psychological disorder, the client application 266 may display a warning or notification to the user and/or may advise the user to see a healthcare professional.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as exemplary only and does not describe every possible embodiment, as describing every possible embodiment would be impractical, if not impossible. One could implement numerous alternate embodiments, using either current technology or technology developed after the filing date of this application.

We claim:

1. A method for identifying biometric characteristics of a user based on audiovisual data, the method executed by one or more processors programmed to perform the method, the method comprising:
   obtaining, at one or more processors, a plurality of sets of audiovisual data corresponding to a plurality of people and one or more biometric characteristics for each of the plurality of people;
   for each of the one or more biometric characteristics:
   analyzing, by the one or more processors, each of the plurality of sets of audiovisual data to identify a plurality of features;
   analyzing, by the one or more processors, the plurality of features in each set of audiovisual data to identify movement data corresponding to changes in the plurality of features over time; and
   generating, by the one or more processors a model for determining an unknown biometric characteristic of a user based on the plurality of features, the movement data, and the obtained biometric characteristic for each of the plurality of people;
   receiving, at the one or more processors, a set of audiovisual data corresponding to a user, wherein the audiovisual data includes a plurality of frames captured over a threshold time period;
   applying, by the one or more processors, features within the set of audiovisual data corresponding to the user to the one or more models to determine the one or more biometric characteristics of the user; and
   providing, by the one or more processors, an indication of the determined one or more biometric characteristics of the user to a client computing device.

2. The method of claim 1, further comprising:
   determining, by the one or more processors, an individual health indicator for each of the one or more determined biometric characteristics of the user; and
   combining, by the one or more processors, the individual health indicators for the user to generate an overall health indicator, wherein providing the indication of the determined one or more biometric characteristics of the user to the client computing device includes providing the overall health indicator to the client computing device.

3. The method of claim 2, wherein the overall health indicator is used to predict remaining longevity for the user.

4. The method of claim 1, wherein analyzing the plurality of sets of audiovisual data to identify a plurality of features includes:
   analyzing, by the one or more processors, each frame in the plurality of sets of audiovisual data to identify a portion of each frame depicting a face of the person using face detection techniques; and
   analyzing, by the one or more processors, the plurality of portions depicting faces to identify a plurality of feature vectors corresponding to the faces.

5. The method of claim 1, wherein the model for determining an unknown biometric characteristic of a user is generated using one or more machine learning techniques.

6. The method of claim 1, wherein the one or more biometric characteristics include at least one of: age, gender, body mass index (BMI), heart rate, body temperature, galvanic skin response (GSR), smoking status, or emotional state.

7. A server computing device for identifying biometric characteristics of a user based on audiovisual data, the server computing device comprising:
   one or more processors; and
   a non-transitory computer-readable memory coupled to the one or more processors, and storing thereon instructions that, when executed by the one or more processors, cause the server computing device to:
   obtain a plurality of sets of audiovisual data corresponding to a plurality of people and one or more biometric characteristics for each of the plurality of people;
   for each of the one or more biometric characteristics:
   analyze each of the plurality of sets of audiovisual data to identify a plurality of features;
   analyze the plurality of features in each set of audiovisual data to identify movement data corresponding to changes in the plurality of features over time; and
   generate a model for determining an unknown biometric characteristic of a user based on the plurality of features, the movement data, and the obtained biometric characteristic for each of the plurality of people;
   receive a set of audiovisual data corresponding to a user, wherein the audiovisual data includes a plurality of frames captured over a threshold time period;
   apply features within the set of audiovisual data corresponding to the user to the one or more models to determine the one or more biometric characteristics of the user; and
   provide an indication of the determined one or more biometric characteristics of the user to a client computing device.

8. The server computing device of claim 7, wherein the instructions further cause the server computing device to:
   determine an individual health indicator for each of the one or more determined biometric characteristics of the user; and
   combine the individual health indicators for the user to generate an overall health indicator, wherein providing the indication of the determined one or more biometric characteristics of the user to the client computing device includes providing the overall health indicator to the client computing device.

9. The server computing device of claim 8, wherein the overall health indicator is used to predict remaining longevity for the user.

10. The server computing device of claim 7, wherein to analyze the plurality of sets of audiovisual data to identify a plurality of features, the instructions cause the server computing device to:
    analyze each frame in the plurality of sets of audiovisual data to identify a portion of each frame depicting a face of the person using face detection techniques; and
    analyze the plurality of portions depicting faces to identify a plurality of feature vectors corresponding to the faces.

11. The server computing device of claim 7, wherein the model for determining an unknown biometric characteristic of a user is generated using one or more machine learning techniques.

12. The server computing device of claim 7, wherein the one or more biometric characteristics include at least one of: age, gender, body mass index (BMI), heart rate, body temperature, galvanic skin response (GSR), smoking status, or emotional state.

13. A non-transitory computer-readable memory storing thereon instructions that, when executed by one or more processors, cause the one or more processors to:
obtain a plurality of sets of audiovisual data corresponding to a plurality of people and one or more biometric characteristics for each of the plurality of people;
for each of the one or more biometric characteristics:
analyze the plurality of sets of audiovisual data to identify a plurality of features;
analyze the plurality of features in each set of audiovisual data to identify movement data corresponding to changes in the plurality of features over time; and
generate a model for determining an unknown biometric characteristic of a user based on the plurality of features, the movement data, and the obtained biometric characteristic for each of the plurality of people;
receive a set of audiovisual data corresponding to a user, wherein the audiovisual data includes a plurality of frames captured over a threshold time period;
apply features within the set of audiovisual data corresponding to the user to the one or more models to determine the one or more biometric characteristics of the user; and
provide an indication of the determined one or more biometric characteristics of the user to a client computing device.

14. The non-transitory computer-readable memory of claim 13, wherein the instructions further cause the one or more processors to:
determine an individual health indicator for each of the one or more determined biometric characteristics of the user; and
combine the individual health indicators for the user to generate an overall health indicator, wherein providing the indication of the determined one or more biometric characteristics of the user to the client computing device includes providing the overall health indicator to the client computing device.

15. The non-transitory computer-readable memory of claim 13, wherein to analyze the plurality of sets of audiovisual data to identify a plurality of features, the instructions cause the one or more processors to:
analyze each frame in the plurality of sets of audiovisual data to identify a portion of each frame depicting a face of the person using face detection techniques; and
analyze the plurality of portions depicting faces to identify a plurality of feature vectors corresponding to the faces.

16. The non-transitory computer-readable memory of claim 13, wherein the model for determining an unknown biometric characteristic of a user is generated using one or more machine learning techniques.

17. The non-transitory computer-readable memory of claim 13, wherein the one or more biometric characteristics include at least one of: age, gender, body mass index (BMI), heart rate, body temperature, galvanic skin response (GSR), smoking status, or emotional state.

* * * * *